United States Patent [19]

Rosier

[11] Patent Number: 4,807,643

[45] Date of Patent: Feb. 28, 1989

[54] DIGITAL ELECTRONEUROMETER

[75] Inventor: Randy N. Rosier, Iowa City, Iowa

[73] Assignee: University of Iowa Research Foundation, Iowa City, Iowa

[21] Appl. No.: 408,193

[22] Filed: Aug. 16, 1982

[51] Int. Cl.$^4$ .............................................. A61B 5/05
[52] U.S. Cl. .................................. 128/741; 128/733; 128/421
[58] Field of Search ............................... 128/733–735, 128/741, 421, 774, 782, 905

[56] References Cited

U.S. PATENT DOCUMENTS

| | | | |
|---|---|---|---|
| 2,808,826 | 10/1957 | Reiner et al. | 128/741 |
| 3,364,929 | 1/1968 | Ide et al. | 128/733 X |
| 3,468,302 | 9/1969 | Cowell | 128/734 |
| 3,508,540 | 4/1970 | Cavallar, Jr. et al. | 128/734 |
| 3,810,457 | 5/1974 | Bottcher et al. | 128/741 |
| 3,898,983 | 8/1975 | Elam | 128/741 |
| 4,064,870 | 12/1977 | Dumitrescu et al. | 128/741 |
| 4,088,125 | 5/1978 | Forgione et al. | 128/734 |
| 4,157,087 | 6/1979 | Miller et al. | 128/741 |
| 4,166,452 | 9/1979 | Generales | 128/741 |
| 4,174,706 | 11/1979 | Jankelson et al. | 128/741 |
| 4,291,705 | 9/1081 | Severinghaus et al. | 128/733 |
| 4,387,723 | 6/1983 | Atlee, III et al. | 128/741 X |

OTHER PUBLICATIONS

Leifer et al., "Non invasive Nerve Conduction Latency Spectrum Measurement and Calibration;" *Biomedizinische Technik;* vol. 21, Supplement, 6-1976, pp. 113–114.

Starzak et al., "Action Potential Clamp to Probe the Effectiveness of Space Clamp in Axons;" *IEEE Trans. Biomed. Eng.;* vol. BME-25, No. 2, 3-1978, pp. 201–204.

*Primary Examiner*—Edward M. Coven
*Assistant Examiner*—Angela Sykes
*Attorney, Agent, or Firm*—James C. Nemmers

[57] ABSTRACT

A portable device for simply and quickly measuring nerve conduction velocities in patients so as to assist the physician in diagnosing the onset of conditions that can cause permanent damage to the patient's nerves and muscles. The device is pocket-size, hand-held and battery-operated, and therefore it can be used by the physician on a day to day basis to provide a useful, objective parameter of the patient's clinical progress.

5 Claims, 1 Drawing Sheet

DIGITAL ELECTRONEUROMETER

BACKGROUND OF THE INVENTION

Measurements of nerve conduction velocity in peripheral nerves has long been a valuable diagnostic tool in orthopedic surgery, neurology and other branches of medicine. It is particularly useful in the diagnoses of various nerve compression syndromes. A diminished velocity is abnormal, and suggests nerve damage which may require immediate surgical intervention.

The traditional technique for making nerve conduction velocity measurements is by stimulating the peripheral nerve with an electrical impulse and measuring the elapsed time from the stimulus until an action potential occurs in a muscle innervated by the nerve under examination. By repeating this technique using a more distal stimulation point along the course of the nerve, and by knowing the distance between the two points of stimulation, the nerve conduction velocity can be calculated. In practice, the measurements are made by the use of surface electrodes positioned over the muscle that pick up the signals which are then amplified and displayed on the screen of an oscilloscope. Measurements of the distance between the stimulus and response peaks on the screen of the oscilloscope are then converted to latency times. This established technique for making such measurements is known as electromyography (EMG). EMG is quite accurate, but requires sophisticated equipment and specialized training to operate the equipment. Thus, such tests are quite expensive and require the inconvenience of moving the patient to the place where the equipment is located. Although much information about the nerve's operation is thus obtained, it cannot be used with any frequency nor can it conveniently be used in emergency situations.

There are numerous medical situations in which frequent monitoring of nerve conduction velocities would be of extreme value to the physician, particularly if such measurements could be made at bedside. For example, where trauma to an extremity has caused pressure in a constrictive fascial compartment, progressive irreversible damage to nerves and muscles can result from ischemia unless immediate surgical decompression takes place. Swelling in a plaster cast can cause a similar problem. Current methods of measuring compartment syndrome involve the introduction of wick catheters into the compartment to measure tissue pressures, but these procedures are invasive and frequently unreliable. Since nerve conduction velocity decreases long before permanent damage results from a compartment syndrome, a method of quickly and easily determining the nerve conduction velocity would be of great value in aiding the physician in making crucial decisions in such cases. There is therefore a need for a portable, simple and inexpensive device for measuring nerve conduction velocities on a frequent basis to provide a useful objective parameter of the patient's clinical progress.

SUMMARY OF THE INVENTION

The device of the invention supplies a high voltage low current impulse of short duration to the stimulating electrode. The same impulse triggers a digital counter to begin counting the output of a square wave oscillator. When the muscle responds to the stimulus by contracting, a second or action impulse is picked up at the distal electrode, amplified and processed by a comparator which turns off the counter. A display reads out the elapsed time between the stimulus and the action impulses. Successive stimulus pulses can be applied and accumulated in a memory, and the cumulative latency time averaged to improve accuracy.

The device of the invention also incorporates a variable preamplifier gain so that the threshold response of the comparator can be varied by the user. Thus, the level at which the comparator turns off the digital counter can be reduced to a level where the detected action potential just is enough to trigger the comparator. Any subsequent decrease in the amplitude of the dectected action potential will fail to stop the counter after a stimulus is applied. This provides an extremely sensitive way for monitoring patients with traumatized extremities who might develop compartment syndromes.

Moreover, the device of the invention can be operated in a mode in which needle electrodes placed in muscles pick up muscle fibrillation potentials which are counted by the digital counter over a predetermined period of time, thus giving a quantitative assessment of nerve injury and repair.

DESCRIPTION OF THE PREFERRED EMBODIMENTS OF THE INVENTION

Figure 1:
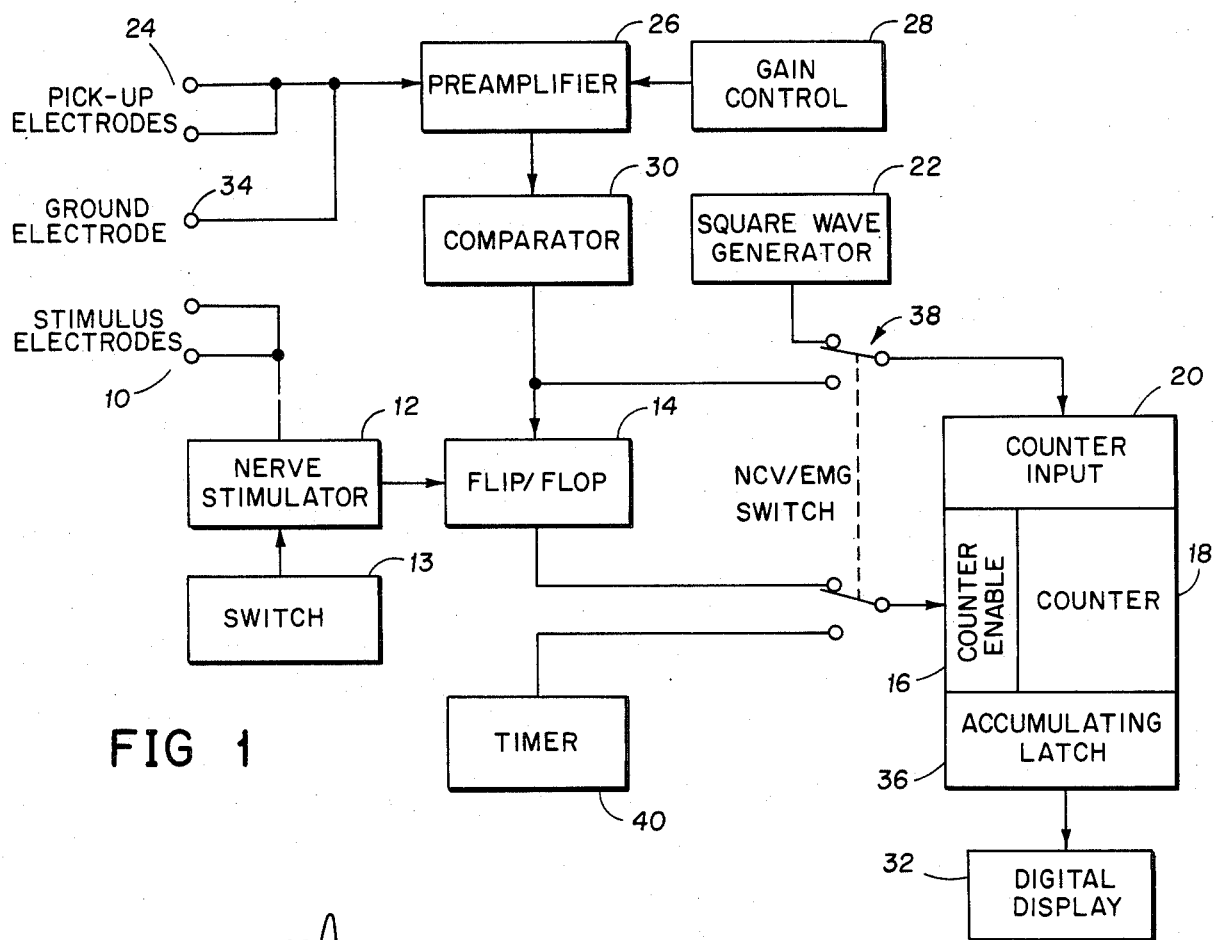
FIG. 1 is a schematic block diagram of the device.

The device of the invention is shown in the schematic diagram of FIG. 1 in which there is illustrated a pair of stimulus electrodes 10 of the surface type connected to a nerve stimulator 12. The nerve stimulator 12 represents any suitable means for supplying a high voltage (e.g. 20-100 volts), low current electrical impulse of less than a millisecond duration to the stimulus electrodes 10. For example, nerve stimulator 12 may include a capacitor charged by a battery through the primary of a transformer which supplies an induced voltage to the electrodes 10 through a variable resistance which would determine the intensity of the stimulus. The stimulator 12 is actuated by an appropriate switch 13 which when closed causes the capacitor to be charged, thus providing the stimulus to the electrodes 10.

Actuation of nerve stimulator 12 would also supply a positive voltage pulse to flip flop 14 which is in turn connected to the counter-enabler 16 of counter 18. The input 20 of counter 18 receives pulses from a square wave generator 22 at a predetermined frequency, e.g. 10 KHz, and when counter-enabler 16 is triggered, counter 18 will commence counting pulses from the generator 22.

The device of the invention also includes a pair of pick-up electrodes 24 of a surface or non-invasive type that are placed on the skin of the patient over a muscle innervated by the nerve which is to be tested. Pick-up electrodes 24 are connected to a preamplifier 26 that has a variable gain control 28.

When a stimulus is supplied to the stimulus electrodes 10 by nerve stimulator 12, this stimulus causes a nerve discharge or action potential to travel distally along the nerve until it reaches the muscle and causes it to contract. When the muscle contracts, the preamplifier 26 will detect the muscle action potential as a potential difference between the two pick-up electrodes 24, amplify the potential difference and supply a signal to the input of a comparator 30. Comparator 30 is preferably an operational amplifier that can be adjusted so that the slightest voltage applied to its input will be amplified at the open loop gain therefore driving the output of the comparator 30 momentarily high. When this occurs, the flip flop 14 will be clocked stopping the counter 18. The elapsed time between the stimulus and muscle contraction will then be displayed in milliseconds on the digital display 32. Thus, if the distance from the stimulus electrodes 10 to the pick-up electrodes 24 is measured, and the measurement repeated at a different point of stimulation, the difference between the two elapsed times and stimulus-response distances can be used to determine the nerve conduction velocity. Preferably, flip flop 14 is configured so that only a single clocking pulse is accepted after the initial triggering thereby preventing multi-phasic action potentials or noise peaks from turning the counter 18 back on until such time as another stimulus is initiated by nerve stimulator 12.

Also, a ground electrode 34 should preferably be affixed to the skin of the patient on the extremity being tested in order to prevent noise pickup by the preamplifier 26. It is also preferable that the power supply for the preamplifier 26 and comparator 30 be separate from the power supply to the remaining circuitry in order to prevent noise from the counting circuits from interfering with the extremely sensitive comparator 30.

In use, the physician will place and affix with tape the surface pick-up electrodes 24 with the attached preamplifier 26 over a muscle innervated by the nerve in question and distal to the point above the nerve to be stimulated. The stimulus electrodes 10 are then held over the nerve at the desired point of stimulus. If desired, the electrodes 10 can be left in place for intermittent monitoring of acute nerve compression syndromes since this insures maximum accuracy for measurement. If disposable electrodes are used, they can be applied under a plaster cast on patients at risk for post operative compartment syndrome, thereby providing periodic monitoring of the nerve conduction velocity in such patients.

Figure 2:
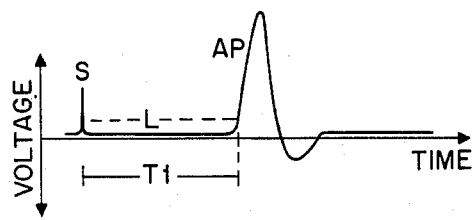
FIG. 2 is a diagram illustrating the changes in potential that occur during use of the device of the invention.

FIG. 2 illustrates the voltage output of the preamplifier 26 versus time. At the point of stimulus, S, the counter 18 is enabled and counts elapsed tenths of milliseconds. In FIG. 2, L represents the gain level set on the preamplifier 26 which will trigger the comparator 30 to stop the counter 18. When the muscle is stimulated and contracts, it causes the appearance of a voltage on the skin called the action potential which is designated AP in FIG. 2. This is typically biphasic in nature having a positive and negative voltage potential as shown. When the positive portion of the action potential voltage reaches the preset level L, the counter 18 is triggered to stop and the count displayed on digital display 32 represents the elapsed time T1 between stimulus and response.

Figure 3:
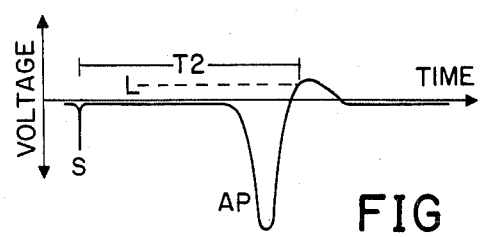
FIG. 3 is a diagram similar to FIG. 2 and illustrating negative potential change which is dependent upon electrode placement.

Since the polarity of the observed action potential is dependent entirely on electrode placement, it may be initially negative in deflection. This is shown in FIG. 3. In this instance, the comparator 30 will not trigger the counter 18 to stop until the positive component of the action potential reaches level L thus giving a longer time T2 which is the sum of the latency time T1 and the duration of the initial phase of the action potential AP. Thus, when actually determining latency times in a patient, it is preferable to use an electrode polarity reversing switch (not shown) to determine the latency time with the electrodes in both the position of initial application and in reverse position with the shorter of the two times representing the true latency time. However, the difference between the two times T1 and T2 is the duration of the depolarization phase of the muscle which is another piece of useful information relevant in certain pathological states.

Figure 5:
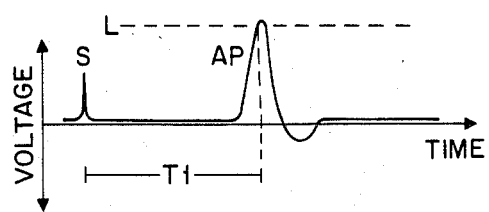
FIGS. 5 and 6 are diagrams which illustrate another mode of the device used to monitor the amplitude of the action potential at the muscle site.
Figure 6:
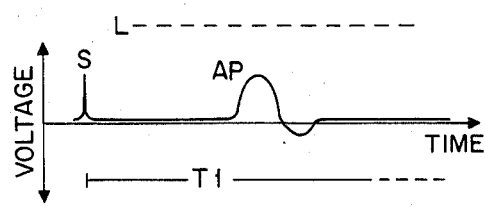

FIGS. 5 and 6 illustrate an important use of the variable gain control of 28 for the preamplifier 26. In certain pathological conditions where close monitoring of nerve activity is necessary (e.g. pending compartment syndrome in traumatized extremities), the gain level L may be set by gain control 28 so that the peak response of the normal action potential AP is just enough to trigger stoppage of the counter 18. This is illustrated in FIG. 5. Since it is customary to determine the latency time T1 from the beginning of the action potential AP, the latency times are not really accurate when the gain level L is set by control 28 so that the peak response of the action potential AP is just enough to trigger stoppage of the counter 18. However, the most sensitive indicator of nerve damage in conditions such as compartment syndrome is a drop in voltage of the action potential after the counter 18 has been enabled by application of a stimulus. With a gain level L set at the peak response of the normal action potential, the clinician may use the device of the invention at such a setting as an extremely sensitive monitoring tool for possible development of post-traumatic nerve compression. FIG. 6 illustrates the situation of a decreasing action potential voltage which never attains the gain level L, and thus the counter 18 continues to run after the stimulus is applied indicating a neurologic deficit.

I also prefer to provide in the device of my invention an accumulating latch 36 on counter 18. This permits the stimulus pulses counted by counter 18 to be accumulated in a memory and the cumulative latency time of successive stimuli averaged thereby improving the accuracy of measurement of the latency time.

Figure 4:
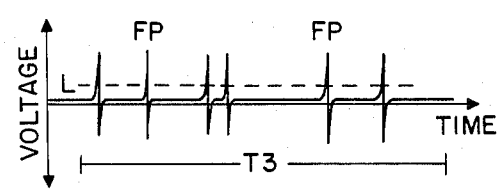
FIG. 4 is a diagram illustrating a mode of the device used to detect electromyographic muscle action potentials.

In a second mode, the device of the invention can be used to detect electromyographic muscle action potentials. In other words, in this second mode, the device will digitally quantitate the number of muscle action potentials occurring under various conditions, e.g., fibrillation potentials in denervated or partially denervated muscle. This mode is valuable in following nerve regeneration after nerve trauma or repair. In this second embodiment, the device is provided with a switch 38 which can be used to shunt the incoming action pulse from the preamplifier 26 directly to the counter 18 and simultaneously connect to counter 18 a timer 40 which has a time constant T3 (FIG. 4). Thus, when the device of the invention is triggered by switch 13, counter 18 will be enabled for a predetermined period of time, say 10 seconds. In this mode of operation, the pick-up electrodes 24 are connected to fine electromyographic needles placed in the muscle being monitored. Therefore, any spontaneous action potentials in the resting muscle (fibrillation potentials) will be counted and displayed on the digital display 32. This is illustrated in FIG. 4 which shows the threshold level L of the preamplifier 26 set by control 28 to determine the cutoff voltage below which pulses are not counted in order to screen out noise and artifacts. The fibrillation potentials FP, which are spontaneous action potentials occurring in denervated or damaged muscle, are counted by counter 18 for the fixed period of time T3. The readout on the digital display 32 thus displays the abnormal muscle activity in terms of number of fibrillation potentials per second which provides an index of the degree of the muscle denervation.

In this second embodiment or mode, the accumulating latch 36 can also be used to accumulate counts over several determinations thus providing the capability of averaging the results of sequential determinations to enhance accuracy. Of course, in either mode the digital display 32 and accumulating latch 36 can be cleared after a single determination if averaging is not desired.

From the foregoing description, it will be evident to those skilled in the art that I have provided a device which is simple, inexpensive and can be used clinically at bedside as an easily repetitive early warning or a screening technique of various nerve and muscle conditions. Sensory, as well as motor nerve conduction velocities, can be measured with the device of the invention because of its high gain capability. It will be further evident to those skilled in the art that although I have illustrated my invention in connection with the preferred embodiments described herein, that various revisions and modifications can be made to the preferred embodiments without departing from the spirit and scope of the invention. It is my intention however that all such revisions and modifications as well as further uses for the device as are obvious to those skilled in the art will be included within the scope of the following claims.

What is claimed is:

1. An apparatus used in determining motor and sensory peripheral nerve conduction potentials in patients, said apparatus comprising first patient contact means for applying an electrical stimulus directly to a selected peripheral nerve of the patient, second patient contact means for electrically detecting a potential difference in a muscle innervated by the nerve stimulated by the first patient contact means, means for producing a stimulus of a low-current electrical impulse of extremely short duration in the first patient contact means, measuring means for determining the elapsed time from a stimulus applied by the first patient contact means to the response detected by the second patient contact means, and means providing for selection of a predetermined threshold level of response detected by said second patient contact means, said measuring means being enabled upon production of the stimulus and disabled by detection of a response above the predetermined threshold level by the second patient contact means.

2. The apparatus of claim 1 in which the measuring means includes a pulse generator for producing pulses of a fixed duration and a counter which counts the output of the generator.

3. The apparatus of claim 2 in which the counter includes an accumulating means for adding the counts of successive measurements.

4. The apparatus of claim 2 in which there is provided a timer for enabling and disabling the counter, and switch means for activating the timer and simultaneously deactivating the pulse generator.

5. The apparatus of claim 1 in which the first and second patient contact means are non-invasive electrodes.

* * * * *